United States Patent
Konno

(10) Patent No.: US 8,836,776 B2
(45) Date of Patent: Sep. 16, 2014

(54) ENDOSCOPE APPARATUS

(71) Applicant: Olympus Medical Systems Corp., Tokyo (JP)

(72) Inventor: Mitsujiro Konno, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/799,391

(22) Filed: Mar. 13, 2013

(65) Prior Publication Data

US 2013/0229505 A1   Sep. 5, 2013

Related U.S. Application Data

(63) Continuation of application No. PCT/JP2012/069251, filed on Jul. 27, 2012.

(30) Foreign Application Priority Data

Sep. 29, 2011   (JP) ................. 2011-214861

(51) Int. Cl.
| | |
|---|---|
| *A62B 1/04* | (2006.01) |
| *A61B 1/06* | (2006.01) |
| *A61B 1/00* | (2006.01) |
| *G02B 23/24* | (2006.01) |
| *A61B 1/04* | (2006.01) |
| *G02B 7/38* | (2006.01) |

(52) U.S. Cl.
CPC ............... *A61B 1/00163* (2013.01); *A61B 1/06* (2013.01); *G02B 7/38* (2013.01); *A61B 1/0005* (2013.01); *A61B 1/0638* (2013.01); *G02B 23/2423* (2013.01); *G02B 23/2484* (2013.01); *A61B 1/04* (2013.01)
USPC .......... 348/65; 348/46; 348/68; 348/E13.074; 382/106; 359/464

(58) Field of Classification Search
CPC .... A61B 1/0005; A61B 1/00163; A61B 1/04; A61B 1/06; A61B 1/0638; A61B 1/00; G02B 23/2423; G02B 23/2484; G02B 7/38; G02B 23/24; G02B 23/26
USPC ..................................................... 348/65, 68
See application file for complete search history.

(56) References Cited

U.S. PATENT DOCUMENTS

| | | | |
|---|---|---|---|
| 6,466,815 B1 * | 10/2002 | Saito et al. ............... | 600/429 |
| 2007/0046778 A1 * | 3/2007 | Ishihara et al. ............ | 348/68 |

(Continued)

FOREIGN PATENT DOCUMENTS

| | | |
|---|---|---|
| JP | 05-153467 | 6/1993 |
| JP | 05-181057 | 7/1993 |

(Continued)

OTHER PUBLICATIONS

F. Guichard, et al., "Extended depth-of-field using sharpness transport across color channels," DxO Labs, Boulogne, France (2009).

(Continued)

*Primary Examiner* — Sath V Perungavoor
*Assistant Examiner* — Dakshesh Parikh
(74) *Attorney, Agent, or Firm* — Kenyon & Kenyon LLP

(57) ABSTRACT

There is provided an endoscope apparatus capable of stably and precisely measuring a distance to an object by suppressing variations in measured values of the distance to the object depending on the presence or absence of pigment dispersion or the like and capable of enabling observations based on clear and high quality images. The endoscope apparatus includes an optical system that condenses light from an object and simultaneously forms two optical images having the same characteristics with difference only in focal point; an imaging element that captures the two optical images formed by the optical system and acquires two images; and a calculation unit that obtains distance information corresponding to a distance to the object based on a contrast ratio of the two images in a range in which the two images acquired by the imaging element have a common contrast.

8 Claims, 6 Drawing Sheets

(56) References Cited

U.S. PATENT DOCUMENTS

| | | | |
|---|---|---|---|
| 2007/0165306 A1* | 7/2007 | Bendall et al. | 359/464 |
| 2007/0203394 A1* | 8/2007 | Wiklof | 600/109 |
| 2010/0046802 A1* | 2/2010 | Watanabe et al. | 382/106 |

FOREIGN PATENT DOCUMENTS

| | | | |
|---|---|---|---|
| JP | 2002-112952 | 4/2002 | |
| JP | 2002-153421 | 5/2002 | |
| JP | 2005-094467 | 4/2005 | |
| JP | 2006-288432 | 10/2006 | |
| JP | 2007-199668 | 8/2007 | |
| JP | 2008-532449 | 8/2008 | |
| JP | 2011-019693 | 2/2011 | |
| KR | 929569 B1 * | 12/2009 | B60R 1/08 |

OTHER PUBLICATIONS

International Search Report, dated Oct. 23, 2012, issued in corresponding International Application No. PCT/JP2012/069251.

* cited by examiner

US 8,836,776 B2

ENDOSCOPE APPARATUS

CROSS-REFERENCE TO RELATED APPLICATIONS

This is a continuation of International Application PCT/JP2012/069251, with an international filing date of Jul. 27, 2012, which is hereby incorporated by reference herein in its entirety. This application claims the benefit of Japanese Patent Application No. 2011-214861, the content of which is incorporated herein by reference.

TECHNICAL FIELD

The present invention relates to an endoscope apparatus.

BACKGROUND ART

There has been known a technique in which chromatic aberration is intentionally generated in an RGB camera to acquire an R image, a G image, and a B image that are shifted in the image forming position and a difference in modulation transfer function (MTF) of each image is converted to distance information to perform auto focus (for example, see PTL 1).

CITATION LIST

Patent Literature

{PTL 1}
Japanese Translation of PCT International Application, Publication No. 2008-532449

SUMMARY OF INVENTION

Technical Problem

The technique according to PTL 1 intentionally generates chromatic aberration, which produces bad quality of RGB images to be acquired, and thus the acquired RGB images cannot be used to observe an object in detail. In an endoscope, even if the distance to the object is the same, contrast information of each RGB varies, for example, depending on the presence or absence of pigment dispersion, and thus the technique according to PTL 1 causes the measured distance values to vary widely, thereby preventing precise observation.

In view of the above circumstances, an aspect of the present invention has been made, and an object thereof is to provide an endoscope apparatus capable of stably and precisely measuring a distance to an object by suppressing variations in measured values of the distance to the object depending on the presence or absence of pigment dispersion or the like and capable of enabling observations based on clear and high quality images.

Solution to Problem

An aspect of the present invention is an endoscope apparatus comprising an optical system that condenses light from an object and simultaneously forms two optical images having the same characteristics with difference only in focal point; an imaging element that captures the two optical images formed by the optical system and acquires two images; and a calculation unit that obtains distance information corresponding to a distance to the object based on a contrast ratio of the two images in a distance range in which the two images acquired by the imaging element have a common contrast.

Advantageous Effects of Invention

The aspect of the present invention exerts an effect capable of stably and precisely measuring the distance to the object by suppressing variations in measured values of the distance to the object depending on the presence or absence of pigment dispersion or the like and capable of enabling observations based on clear and high quality images.

DESCRIPTION OF EMBODIMENTS

Figure 1:
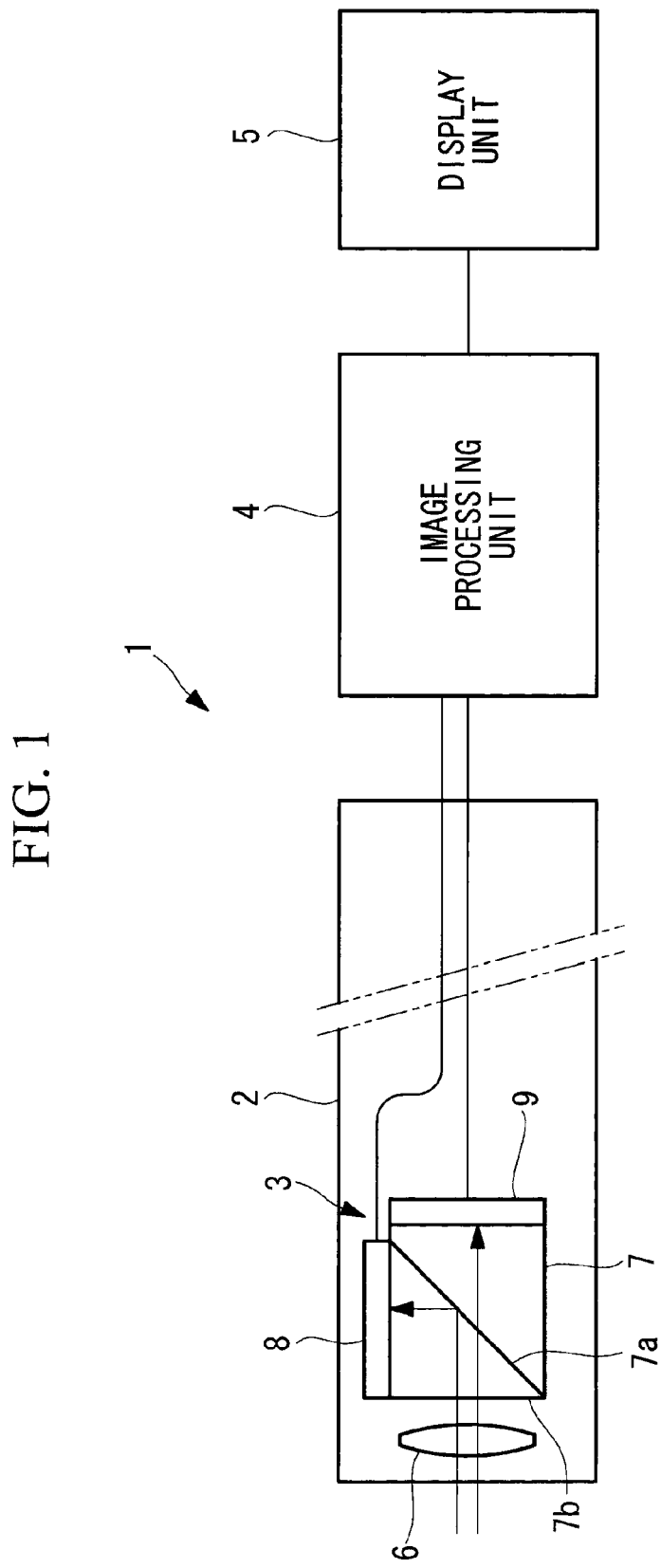
FIG. 1 is an entire configuration view illustrating an endoscope apparatus according to an embodiment of the present invention.

According to an aspect of the present invention, when light from an object is incident on an optical system, two optical images having the same characteristics with difference only in focal point are formed, and two formed optical images are captured by an imaging element, and thereby two images are acquired. The two images are different in the focal point of the optical image, and thus have different contrast for each pixel. Thus, a calculation unit can easily obtain distance information corresponding to the distance to the object based on the contrast ratio thereof.

In this case, the two images used to obtain the distance information are acquired by capturing the two optical images having the same characteristics with difference only in focal point. Thus, the changes of the two images depending on the presence or absence of pigment dispersion are the same and the distance information obtained based on the contrast ratio of the two images does not change. In addition, the two images acquired from the two optical images having the same characteristics with difference only in focal point have higher image quality than conventional images acquired by intentionally generating chromatic aberration. Thus, the viewer can observe the object in detail based on clear images.

A configuration may be such that the calculation unit stores a map associating a contrast ratio of the two images with distance information and obtains the distance information from the map using the contrast ratio of the two images.

This configuration can use the map to easily determine the relation between the contrast ratio of the two images and the distance information, which is difficult to be represented by an approximate expression, and thus can easily and quickly obtain the distance information corresponding to the distance to the object from the contrast ratio.

A configuration may be such that the two optical images formed by the optical system overlap in a range of 10% or more of a modulation transfer function in a frequency corresponding to a maximum resolution.

This configuration can obtain an accurate contrast ratio from a contrast in a range where the two images have a common and sufficient modulation transfer function, and thus can obtain the distance information corresponding to the accurate distance based on the contrast ratio.

A configuration may comprise an image synthesizing unit that generates a composite image by adopting pixel information having a higher contrast from the two images acquired by the imaging element; and a display unit that displays both the composite image generated by the image synthesizing unit and the distance information obtained by the calculation unit.

This configuration makes the composite image generated by the image synthesizing unit into an image having depth of focus deeper than the depth of focus of each image, and thus the viewer can observe the object in detail based on a clear image in focus over a wide range. This configuration displays both the composite image and the distance information on the display unit, and thereby the viewer can easily understand the size of the object.

This configuration may comprise a characteristics processing unit that performs a process of varying display characteristics of both images on at least one of the two images acquired by the imaging element, wherein the image synthesizing unit synthesizes the two images subjected to the process provided by the characteristics processing unit; and the display unit displays both the composite image generated by the image synthesizing unit and the distance information at a boundary position between the two images.

In this configuration, the characteristics processing unit synthesizes the two images varying in display characteristics and thereby the boundary position between the two images becomes clear in the composite image displayed on the display unit. In addition, the distance information at this boundary position is displayed together with the composite image, and thereby the viewer can easily understand the size of the object at the boundary position.

This configuration may be such that the optical system comprises a light condensing optical system that condenses a light beam from the object and a branching optical system that branches the light beam condensed by the light condensing optical system, wherein the imaging element is disposed at a different position from a branch point by the branching optical system in an optical axis direction.

This configuration can easily form two optical images having the same characteristics with difference only in focal point and can easily acquire two images from the two optical images formed as such.

Hereinafter, an endoscope apparatus 1 according to an embodiment of the present invention will be described with reference to the accompanying drawings.

As illustrated in FIG. 1, the endoscope apparatus 1 according to the present embodiment includes an imaging unit 3 disposed at a front end of an elongated insertion unit 2 to be inserted into an observation target; an image processing unit 4 connected to the imaging unit 3; and a display unit 5 for displaying an image processed by the image processing unit 4.

The imaging unit 3 is disposed at a front end of the insertion unit 2 and includes an object lens 6 for condensing a light beam from an object, a half prism 7 for branching the light beam condensed by the object lens 6 into two light beams, and two imaging elements 8 and 9 fixed so as to arrange an imaging surface on side surfaces orthogonal to each other of the half prism 7.

The half prism 7 has a semi-transparent surface 7a oriented at an angle of 45° with respect to the optical axis of the object lens 6. The semi-transparent surface 7a reflects half of the incident light beams and transmits the other half of the light beams. The half prism 7 is dimensioned to vary the distance along the optical axis from the incident surface 7b on which the light beams from the object condensed by the object lens 6 are incident on the two lateral surfaces fixing the imaging elements 8 and 9 respectively.

Figure 2:
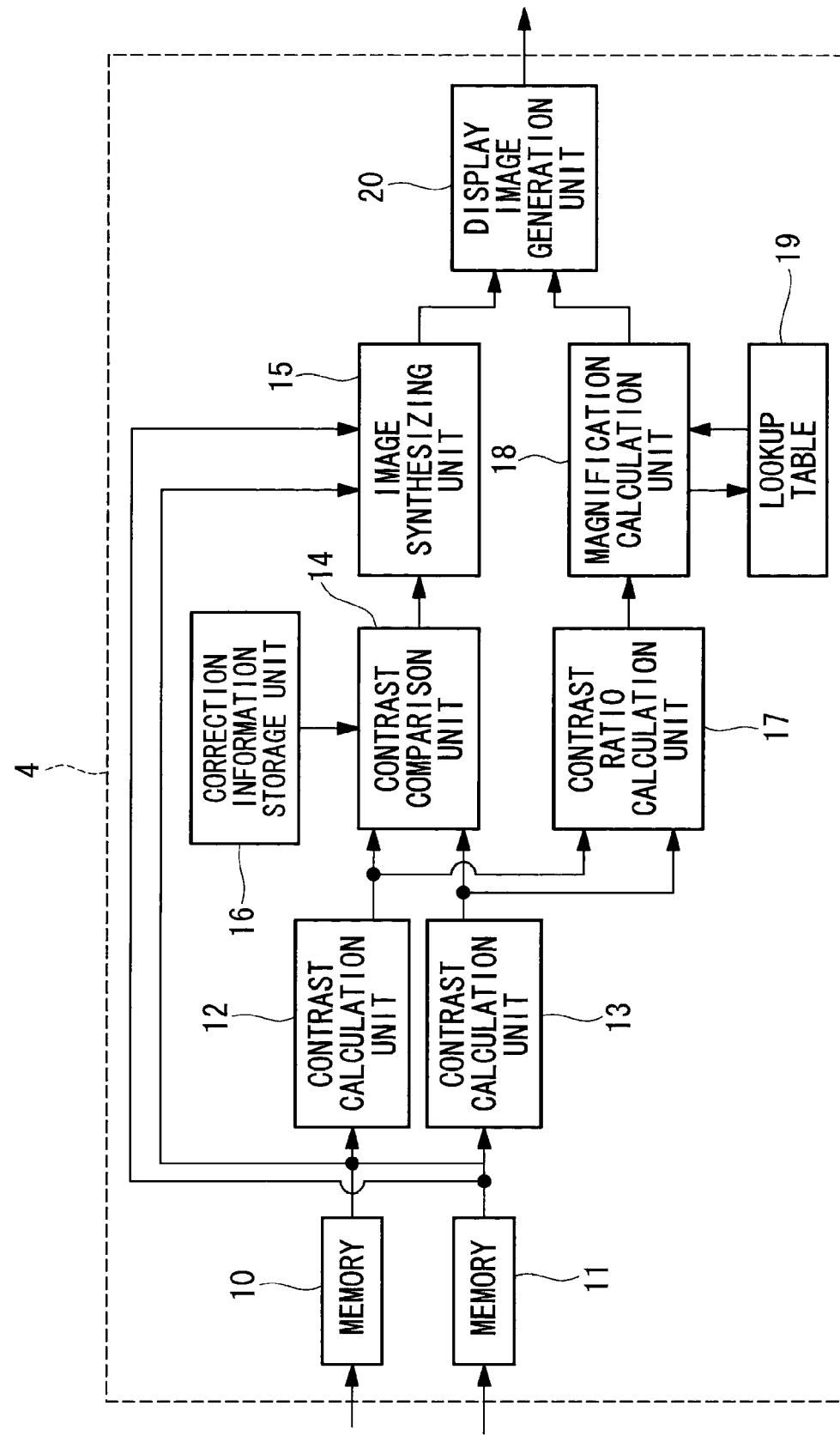
FIG. 2 is a functional block diagram illustrating an image processing unit of the endoscope apparatus in FIG. 1.

As illustrated in FIG. 2, the image processing unit 4 includes two memories 10 and 11 for storing image information outputted from the two imaging elements 8 and 9 respectively; contrast calculation units 12 and 13 for calculating contrast values from image information stored in the memories 10 and 11 respectively; a contrast comparison unit 14 for comparing the contrast values of the two images for each pixel corresponding to the same coordinate; and an image synthesizing unit 15 for generating a composite image by adopting an pixel value of an image having a larger contrast value as a result of comparison.

The contrast calculation units 12 and 13 are configured to calculate a modulation transfer function (MTF) in a Nyquist frequency of the imaging elements 8 and 9 as contrast values.

The contrast comparison unit 14 is connected to a correction information storage unit 16 for storing correction information for correcting a positional shift specific to the half prism 7 and the imaging elements 8 and 9 so as to match the coordinates of each pixel for comparing the contrast values. Upon comparison, the contrast comparison unit 14 compares the contrast values of each pixel having exactly the same coordinates by referring to the correct information stored in the correction information storage unit 16.

The image processing unit 4 further includes a contrast ratio calculation unit 17 for calculating a ratio of the contrast values in an image center calculated by the contrast calculation units 12 and 13; and a magnification calculation unit 18 for calculating a magnification based on the calculated contrast ratio. The magnification calculation unit 18 is connected to a map storage unit 19 that stores a lookup table (map) associating the contrast ratio with the magnification (distance information) so as to search the lookup table for a magnification corresponding to the contrast ratio inputted from the contrast ratio calculation unit 17.

Figure 4:
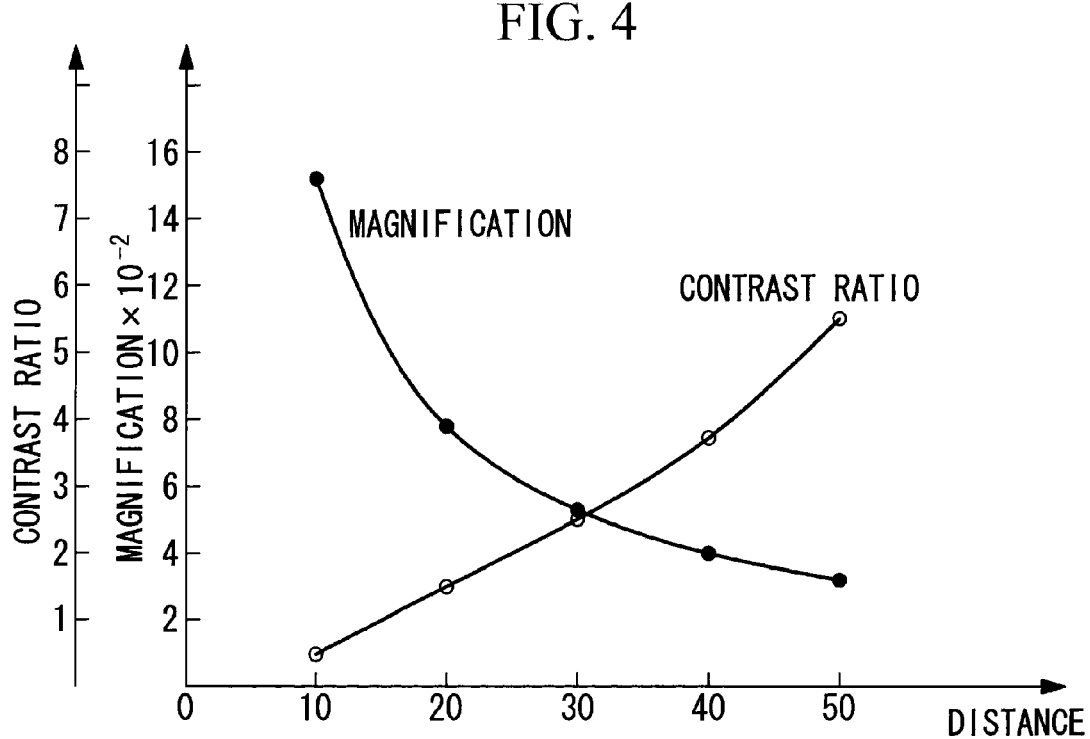
FIG. 4 is a graph illustrating a relation between the image distance and the contrast ratio as well as the distance and a magnification thereof.
Figure 5:
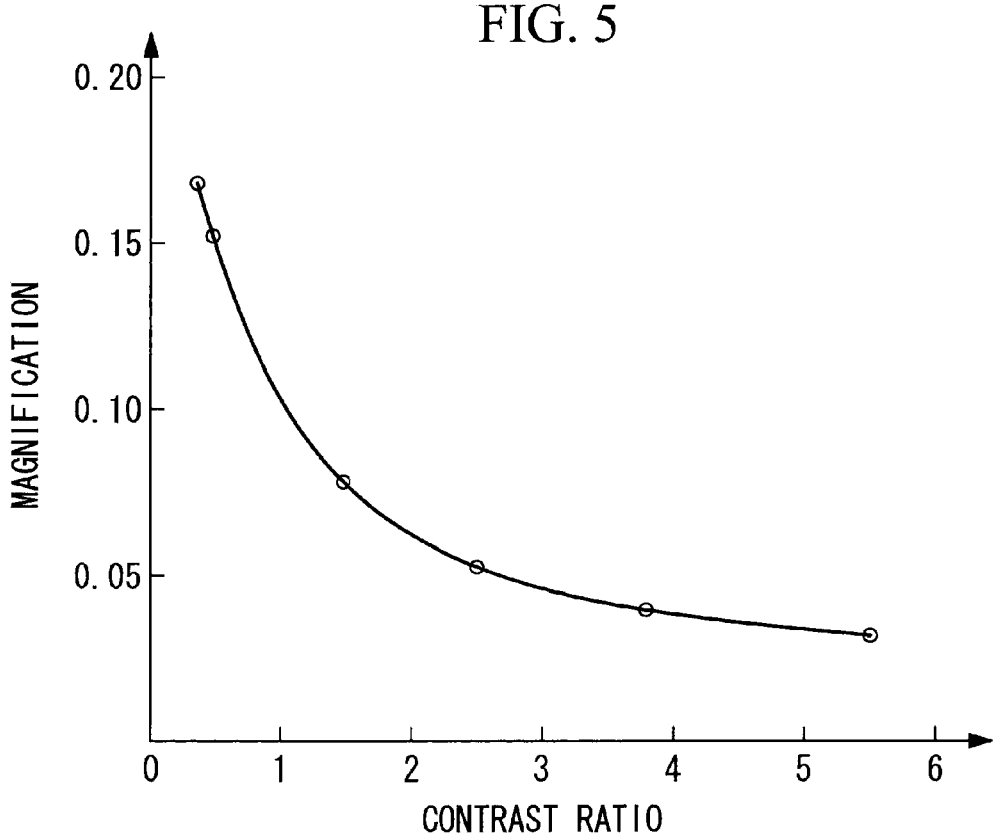
FIG. 5 is an example of a lookup table illustrating a relation between a contrast ratio stored in a map storage unit of the endoscope apparatus in FIG. 1 and a magnification thereof.

Specifically, as illustrated in FIG. 4, the relation between the distance and the contrast ratio as well as the relation between the distance and the magnification can be preliminarily obtained. Thus, as illustrated in FIG. 5, the relation between the contrast ratio and the magnification can also be preliminarily obtained. Since it is difficult to define an approximation curve indicating the relations with a mathematical equation, it is practical to store the relation in the lookup table.

Figure 3:
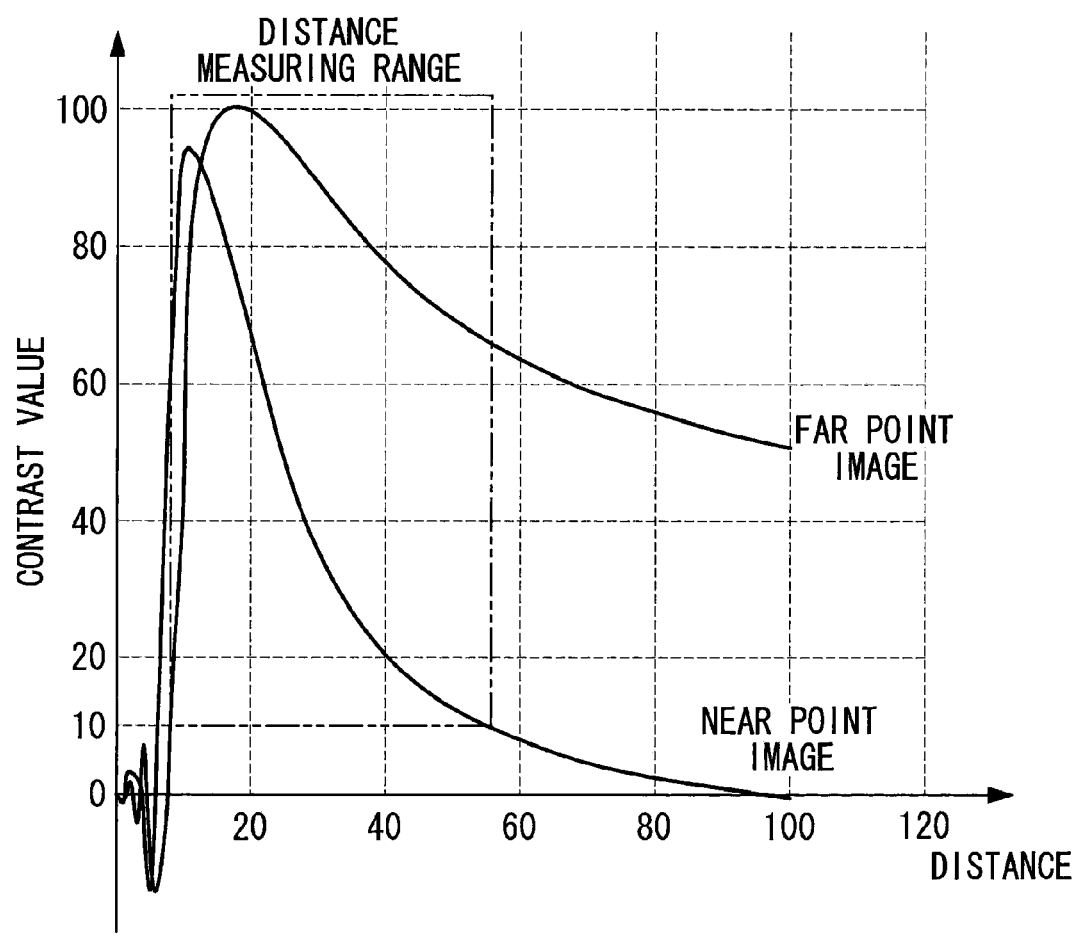
FIG. 3 is a graph illustrating a relation between a contrast value of two images acquired by two imaging elements of the endoscope apparatus in FIG. 1 and a distance of each thereof.

The contrast ratio calculation unit 17 is configured to calculate the ratio of two contrast values as a contrast ratio in a range where the contrast values of the two images in a center of the screen are equal to or greater than 10% as illustrated in FIG. 3.

The image processing unit 4 further includes a display image generation unit 20 that uses the composite image generated by the image synthesizing unit 15 and the magnification calculated by the magnification calculation unit 18 to generate a display image to be displayed on the display unit 5.

Figure 6:
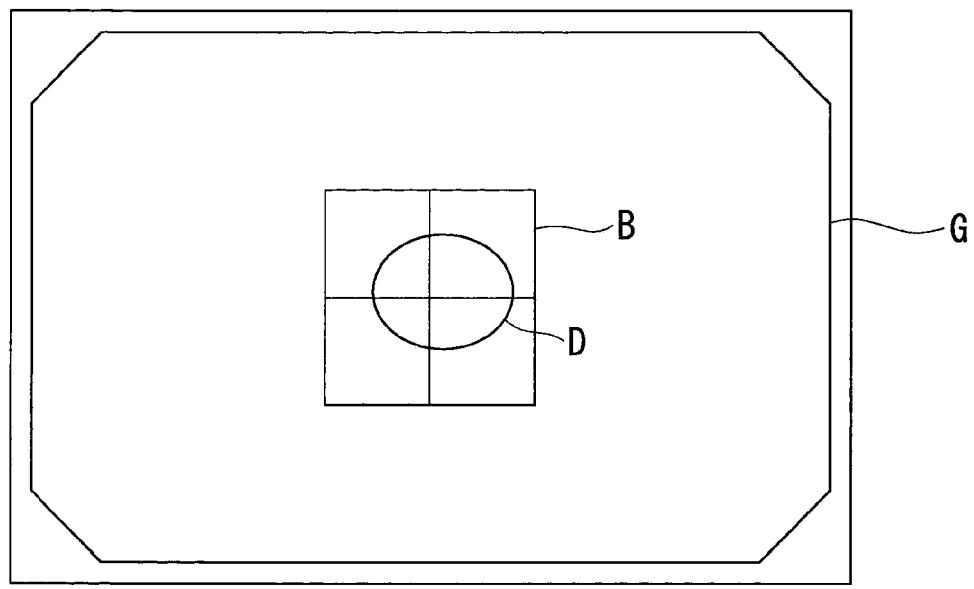
FIG. 6 is an example of an image displayed by a display unit of the endoscope apparatus in FIG. 1.

Specifically the display image generation unit 20 displays the magnification calculated by the magnification calculation unit 18 in the composite image using a numerical character, or as illustrated in FIG. 6, displays a reference scale B, for example, a frame or a gauge with a side of 10 mm, in a size corresponding to the magnification, in a center of the composite image G.

Now, an operation of such configured endoscope apparatus 1 according to the present embodiment will be described.

When an object is observed using the endoscope apparatus 1 according to the present embodiment, the front end of the insertion unit 2 is placed so as to face the object and a light beam from the object is condensed by the object lens 6. The condensed light beam is incident on the incident surface 7b of the half prism 7 and branches into two light beams on the semi-transparent surface 7a. One light beam reflected on the semi-transparent surface 7a passes along a short optical path and is incident on the imaging element 8. The other light beam transmitted through the semi-transparent surface 7a passes along a long optical path and is incident on the imaging element 9.

Thereby, two optical images having the same characteristics with difference only in focal point are formed on the imaging surfaces of the two imaging elements 8 and 9. Then, respective optical images are captured separately by the two imaging elements 8 and 9, and two images are acquired. Image information outputted from each of the imaging elements 8 and 9 is inputted to the image processing unit 4, and is stored separately in the memories 10 and 11 respectively. Then, a contrast value is calculated for each pixel by the contrast calculation units 12 and 13.

The contrast values of pixels arranged on the same coordinate of the two images are inputted to the contrast comparison unit 14 for comparison. Then, the image synthesizing unit 15 generates a composite image by adopting a pixel value of a pixel having a higher contrast value. This makes it possible to obtain a clear image in focus over a wide range from a near point to a far point.

The contrast value of the pixel arranged on the same coordinate in a center of each image is sent to the contrast ratio calculation unit 17. If all the sent contrast values exceed 10%, the contrast ratio calculation unit 17 calculates a contrast ratio.

If a contrast ratio is calculated, the calculated contrast ratio is sent to the magnification calculation unit 18, which searches the lookup table stored in the map storage unit 19 for a magnification. Then, the magnification outputted from the magnification calculation unit 18 and the composite image G outputted from the image synthesizing unit 15 are sent to the display image generation unit 20 to generate a display image.

As illustrated in FIG. 6, the display image is located near a center of the composite image G indicated by a reference scale B according to the magnification, and the size of a region-of-interest D located near a center of the composite image G can be easily confirmed by the reference scale B.

As described above, the endoscope apparatus 1 according to the present embodiment obtains the magnification by the contrast ratio, and thus can stably and precisely measure a distance to an object by suppressing variations in measured values of the distance to the object with pigment dispersion or the like. Thus, the viewer can observe the object based on clear and high quality images.

In particular, the endoscope apparatus 1 according to the present embodiment also has advantages in that the size of an object can be confirmed without providing a special distance measuring means while observing the object based on a clear image in focus over a wide range from a near point to a far point and the size of apparatus can be simplified and reduced.

Figure 7:
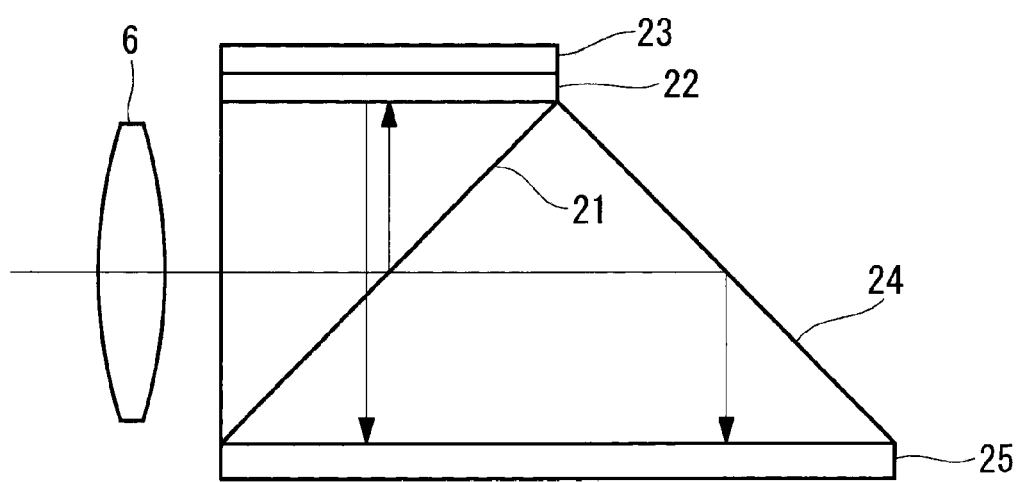
FIG. 7 illustrates a modification of an optical system of the endoscope apparatus in FIG. 1.

Note that the present embodiment provides two imaging elements 8 and 9, each of which separately captures each of the two optical images branched by the half prism 7 to acquire two images; alternatively, as illustrated in FIG. 7, a polarizing beam splitter 21, a γ/4 plate 22, a mirror 23, and a prism 24 may be combined to guide the branched two light beams to a single lateral surface of the prism 24, where a single imaging element 25 captures the two optical images in a separate region thereof.

Figure 8:
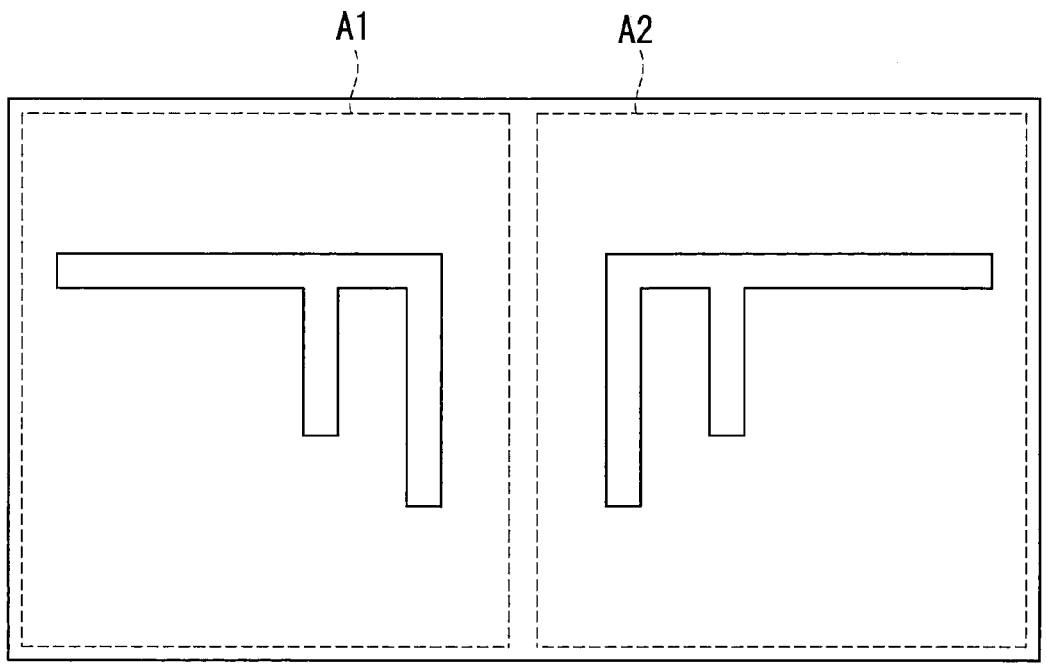
FIG. 8 illustrates an example of an image acquired by the endoscope apparatus according to the present embodiment having the optical system in FIG. 7.

The optical system illustrated in FIG. 7 acquires the images illustrated in FIG. 8. Rotation and magnification correction are performed on areas A1 and A2 of each image, and an image of either one of the areas is inverted to match the two images.

Figure 9:
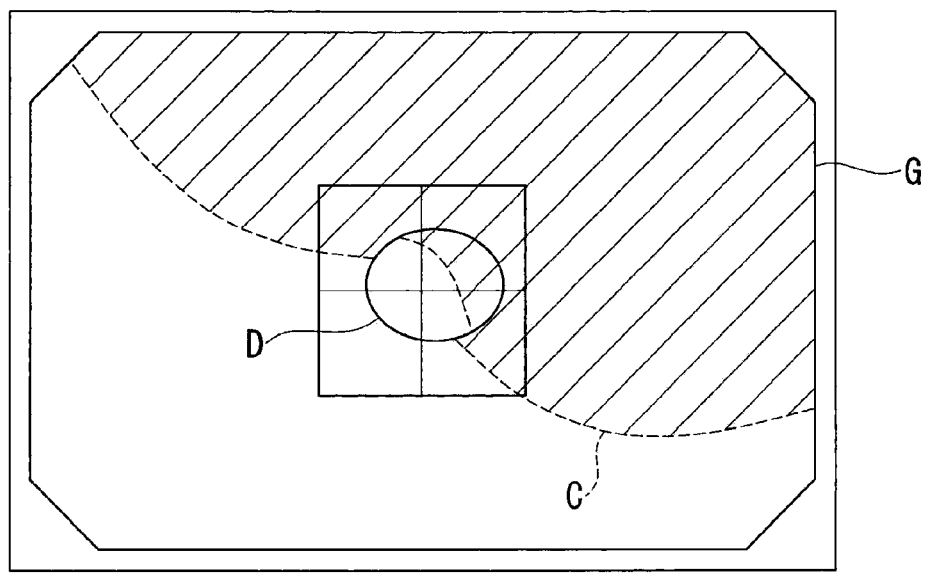
FIG. 9 illustrates an example of an image displayed by the display unit according to the modification of the endoscope apparatus in FIG. 1.

Note also that as illustrated in FIG. 3, the present embodiment makes an adjustment so as to overlap the MTF of the two images over a wider possible range; alternatively, an adjustment may be made so as to overlap the MTF over a narrower possible range, ultimately in a single distance. This configuration clearly divides the areas containing pixels of the two images. Thus, as illustrated in FIG. 9, the display image generation unit 20 can clearly display a boundary line C between the two images on the display image by performing a process of varying the display characteristics of one image.

Examples of the process of varying the display characteristics include changing the brightness of one image and coloring one image.

The process of changing the brightness of one image generates the composite image G with areas different in brightness arranged adjacent to each other.

As described above, the distance on the boundary line C is known beforehand so that the contrast ratio needs not to be calculated. Thus, once the reference scale B indicating the magnification is displayed on the display image, the size of the region-of-interest D arranged in the center of the image can be easily known by moving the insertion unit 2 such that the boundary line C passes through the center of the image.

The present embodiment is configured such that the composite image G is generated by the image processing unit 4 connected to the imaging elements 8 and 9 arranged in the insertion unit 2. Thus, the viewer who operates the endoscope apparatus 1 can know the size of the object in real time during observation.

Alternatively, a configuration may be such that the two images acquired by the imaging elements 8 and 9 are stored in a storage medium and image processing is later performed by a computer which measures the size of the object offline.

The present embodiment is configured such that the magnification calculation unit 18 obtains the magnification corresponding to the distance from the contrast ratio as the distance information; alternatively, the distance itself may be calculated and displayed on the display image.

The contrast ratio is not limited to the value in the MTF, but may be, for example, a ratio of evaluation values related to contrast information using both a low-frequency component and a high-frequency component of the MTF. As described above, even if the MTFs of the two images are overlapped over a narrower possible range, as illustrated in FIG. 3, this configuration can exert an effect equivalent to adjusting to overlap the MTFs of the two images over a wider possible range and can make a sufficiently wide measurable range.

REFERENCE SIGNS LIST 1 endoscope apparatus
5 display unit
6 object lens (light condensing optical system)
8 half prism (optical system, branching optical system)
8, 9, 25 imaging element
15 image synthesizing unit
18 magnification calculation unit (calculation unit)
20 display image generation unit (characteristics processing unit)

The invention claimed is:

1. An endoscope apparatus comprising:
an optical system that forms two optical images having different distances to a focal point in focus of an object;
an imaging element that acquires two images by capturing the two optical images; and
a calculation unit that obtains distance information corresponding to a distance to the object based on a value which is obtained by a comparison process which compares a contrast value of one of the two images and a contrast value of the other of the two images, the comparison process being performed in a distance range in which the two images have a common contrast.

2. The endoscope apparatus according to claim 1, wherein the two optical images formed by the optical system have the same optical characteristics.

3. The endoscope apparatus according to claim 1, wherein the calculation unit stores a map associating the value with distance information and obtains the distance information from the map using the value.

4. The endoscope apparatus according to claim 1, wherein the two optical images formed by the optical system overlap in a distance range of 10% or more of a modulation transfer function in a frequency corresponding to a maximum resolution.

5. The endoscope apparatus according to claim 1, comprising
an image synthesizing unit that generates a composite image by adopting pixel information having a higher contrast from the two images acquired by the imaging element; and
a display unit that displays both the composite image generated by the image synthesizing unit and the distance information obtained by the calculation unit.

6. The endoscope apparatus according to claim 5, comprising a characteristics processing unit that performs a process of varying display characteristics of both images on at least one of the two images acquired by the imaging element, wherein
the image synthesizing unit synthesizes the two images after going through the process provided by the characteristics processing unit; and
the display unit displays both the composite image generated by the image synthesizing unit and the distance information at a boundary position between the two images.

7. The endoscope apparatus according to claim 1, wherein
the optical system comprises a light condensing optical system that condenses a light beam from the object and a branching optical system that branches the light beam condensed by the light condensing optical system; and
the imaging element is disposed at a different position from a branch point by the branching optical system in an optical axis direction.

8. The endoscope apparatus according to claim 1, wherein the imaging element captures the two images simultaneously.

* * * * *